(12) United States Patent
Webler (10) Patent No.: US 6,947,787 B2
(45) Date of Patent: Sep. 20, 2005

(54) SYSTEM AND METHODS FOR IMAGING WITHIN A BODY LUMEN

(75) Inventor: William E. Webler, Escondido, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 405 days.

(21) Appl. No.: 10/029,740

(22) Filed: Dec. 21, 2001

(65) Prior Publication Data

US 2003/0135101 A1 Jul. 17, 2003

(51) Int. Cl.$^7$ ................................................. A61B 6/00
(52) U.S. Cl. ....................... 600/434; 600/407; 600/420; 600/423; 600/424; 600/433; 600/435; 600/466; 600/473; 600/478
(58) Field of Search ................................. 600/407, 420, 600/423, 424, 433, 434, 435, 466, 473, 478, 476, 431; 382/128; 356/349

(56) References Cited

U.S. PATENT DOCUMENTS

| | | | |
|---|---|---|---|
| 4,572,202 A | 2/1986 | Thomenius | |
| 4,743,966 A | 5/1988 | Matsuo | |
| 4,755,889 A | 7/1988 | Schwartz | 360/32 |
| 4,857,990 A | 8/1989 | Horgan | 358/13 |
| 4,918,523 A | 4/1990 | Simon et al. | 358/133 |
| 5,321,501 A | 6/1994 | Swanson et al. | 356/345 |
| 5,459,570 A | 10/1995 | Swanson et al. | 356/345 |
| 5,505,088 A | 4/1996 | Chandraratna et al. | |
| 5,570,182 A | 10/1996 | Nathel et al. | 356/345 |
| 5,582,171 A | * 12/1996 | Chornenky et al. | 600/425 |
| 5,827,176 A | 10/1998 | Tanaka et al. | |
| 5,935,075 A | 8/1999 | Casscells et al. | 600/474 |
| 6,004,280 A | 12/1999 | Buck et al. | 600/585 |

(Continued)

FOREIGN PATENT DOCUMENTS

WO    WO 01/89598 A2    11/2001

OTHER PUBLICATIONS

Brazinski et al., "Optical Coherence Tomography for Optical Biopsy" Circulation 93(6):1206–1213 (Mar. 1996).
Brazinski et al., "Assessing atherosclerotic plaque morphology: comparison of optical coherence tomography and high frequency intravascular ultrasound" Heart 77:397–403 (1997).
Brezinski et al., "Optical Biopsy with Optical Coherence Tomography: Feasibility for Surgical Diagnostics" Journal of Surgical Research 71:32–40 (1997).
Fujimoto et al., "New Technology for High–Speed and High–Resolution Optical Coherence Tomography" Annals New York Acadamy of Sciences 95–107/.
Tearney et al., "Scanning single–mode fiber optic catheter–endoscope for optical coherence tomography" Optics Letters 21(7):543–545 (Apr. 1996).

Primary Examiner—Brian L. Casler
Assistant Examiner—William Jung
(74) Attorney, Agent, or Firm—Fulwider Patton Lee & Utecht, LLP (57) ABSTRACT

Systems, methods and apparatus for acquiring an image from within a body lumen are provided. Systems embodying features of the invention include an intracorporeal imaging component for acquiring imaging information, an image information recording component, and an image information playback component. Methods for acquiring image information from within a body lumen include steps of acquiring imaging information, storing image information, and playing back imaging information. Imaging information may be played back as acquired, or non-sequentially, or composite images may be formed by combining, filtering, enhancing, or subtracting images and the composite images displayed. Devices embodying features of the invention include optical imaging components such as an optical IGW, an optical imaging recording component, and an optical image playback component. The systems, methods and devices are suitable for use with angiopoplasty, stent delivery, and other intracorporeal clinical procedures.

32 Claims, 3 Drawing Sheets

U.S. PATENT DOCUMENTS

| | | | |
|---|---|---|---|
| 6,035,229 A * | 3/2000 | Silverstein et al. | 600/473 |
| 6,111,645 A | 8/2000 | Tearney et al. | 356/354 |
| 6,134,003 A | 10/2000 | Tearney et al. | 356/345 |
| 6,185,367 B1 | 2/2001 | Keery et al. | 386/122 |
| 6,249,551 B1 | 6/2001 | Yamaguchi | 375/240.25 |
| 6,263,234 B1 * | 7/2001 | Engelhardt et al. | 600/476 |
| 6,300,961 B1 | 10/2001 | Finger et al. | 345/505 |
| 6,317,152 B1 | 11/2001 | Hobson et al. | 348/150 |
| 6,400,980 B1 * | 6/2002 | Lemelson | 600/478 |
| 6,445,939 B1 * | 9/2002 | Swanson et al. | 600/342 |
| 6,485,413 B1 * | 11/2002 | Boppart et al. | 600/160 |
| 6,564,087 B1 * | 5/2003 | Pitris et al. | 600/478 |
| 6,668,185 B2 * | 12/2003 | Toida | 600/425 |

* cited by examiner

SYSTEM AND METHODS FOR IMAGING WITHIN A BODY LUMEN

FIELD OF THE INVENTION

The present invention relates generally to intracorporeal instruments for obtaining optical information from within a body lumen. In particular, the invention relates to systems and methods for acquiring and playing optical imaging information obtained from within a body lumen.

BACKGROUND OF THE INVENTION

Intracorporeal devices are devices suitable for introduction into a patient's body, for example, into a body lumen of a patient. Many clinical procedures require the insertion of wires, tubes, probes or other objects into a body lumen of a patient. For example, guidewires and catheters may be used for gaining access to the coronary vasculature, as in an angiogram or in angioplasty. A guidewire is a thin, flexible device used to provide a guiding rail to a desired location within the vasculature (or other body cavity) of a patient. A balloon catheter is a device with an interior lumen with at least a portion of the catheter being able to expand. In coronary angioplasty, a balloon catheter, guided by a guidewire, is positioned within a partially-occluded coronary artery where its balloon portion is expanded in order to press against and enlarge the lumen of a blood vessel in which it is situated. Alternatively, endoscopy requires the introduction of an endoscope into the lumen of a patient, as may be done during a colonoscopy.

Imaging of internal body lumens provides clinicians with information useful in many clinical situations and procedures. Imaging may be accomplished using electromagnetic radiation (such as, e.g., optical radiation, infrared radiation, and radiofrequency radiation). For example, where a patient is suspected of having an occlusion in an artery, optical imaging of the artery and the artery wall can provide information about the type, severity and extent of an occlusion or lesion and so improve the diagnosis and treatment of the patient. Intracorporeal imaging is useful for the placement of guidewires, catheters, endoscopes, and other instruments in desired locations within a patient's body, typically within a body lumen.

The ability to decide where to locate a catheter during a clinical procedure can be improved by providing interior images of the body lumen, such as the blood vessels during angioplasty or the colon during colonoscopy. It is often critical to the success of an angioplasty procedure that a balloon catheter be properly located within a blood vessel. Thus, imaging by guidewire, catheter, or other such device can be of great importance to the success of the procedure.

Imaging endoscopes, guidewires and catheters have been described, as in U.S. Pat. Nos. 5,321,501 and 5,459,570 to Swanson et al., and U.S. Pat. No. 6,134,003 to Tearney et al. Catheters adapted for optical imaging using non-visible light may be useful as well, as disclosed in U.S. Pat. No. 5,935,075 to Cassells et al. Such imaging devices typically use an optical fiber to carry light. Imaging systems may be used to obtain image information from within a body lumen, as discussed by Swanson et al. and Tearney et al., and may be used to obtain image information from peripheral tissues as well, such as teeth, as discussed by Nathel et al., U.S. Pat. No. 5,570,182. All patents and patent applications, both supra and infra, are hereby incorporated by reference in their entirety.

Optical imaging of internal lumens may be performed using endoscopes, guidewires, and catheters. One method useful for optical imaging is termed "optical coherence tomography" (OCT). OCT utilizes optical interference between two halves of a split optical beam to detect small differences in path-length between light reflected from a fixed surface and light reflected from an object to be imaged, as described, e.g., in U.S. Pat. No. 6,134,003 to Tearney et al. OCT may be used with intracorporeal instruments to image within a body lumen. OCT typically uses a short coherence-length light source, and a single-mode optical fiber is typically used to direct and to carry the optical radiation. In addition, an OCT system may include such other components as an interferometer, an optical radiation detector, a reference optical reflector, and a beam director to direct or rotate the optical beam. The beam director may include a prism, a lens, or a mirror.

In OCT, a beam divider is used to divide the optical radiation from an optical radiation source along a first optical path to a reflector and along a second optical path to the structure being viewed. An optical radiation detector is positioned to receive reflected optical radiation from the reflector and reflected optical radiation from the structure and to generate a signal in response to the reflected optical radiation. The signals from the detector may be utilized to generate an image or to obtain other information about the structure being viewed.

An optical fiber or bundle of fibers may be used to carry optical radiation. Optical fibers may be part of an optical assembly, and may be clad or wrapped with other materials for strength and to improve the efficiency of optical transmission. A ferrule may be attached to an end of the optical fiber to strengthen and protect the optical fibers, and to facilitate the attachment of optical fibers to other optical instruments.

An imaging instrument typically has a window to allow optical access between the exterior of the device and an optical fiber or light path within the device. In addition, an optical fiber, or the entire optical instrument, may be rotated within an internal lumen to provide a complete optical scan of a region of the lumen.

The optical path of an optical imaging instrument for use within a body lumen must connect to other instruments in order to pass optical information to other instruments and ultimately to an operator. Thus, the optical path must be configured to operably connect with other optical instrumentation external to the patient's body. Thus, it is often advantageous to have a window in an imaging catheter, imaging guidewire (IGW), endoscope, or other imaging probe to allow optical access between the exterior of the device and the optical fiber or light path within the device. U.S. Pat. No. 6,134,003 to Tearney et al. discloses a rigid plastic clear window.

In coronary angioplasty, a guidewire and an angioplasty catheter are threaded through a patient's vascular bed to bring the distal ends of the guidewire and catheter to and beyond the site of the lesion. For effective use of a balloon angioplasty catheter, the distal end of the balloon angioplasty catheter preferably extends to a position distal to the lesion. For this reason, it is vital that the clinician have accurate knowledge of the extent of the lesion and the condition of the lumen wall.

To do so, the imaging instrument must be located within the body lumen containing the lesion, positioned adjacent or near to the lesion. Typically, an imaging instrument will be advanced distally into the lumen, until a lesion is encountered. The instrument will often be advanced further distally to determine the extent and margins of the lesion, and to position therapeutic instruments across the lesion so that the entire lesion may be treated.

After such distal positioning within a lumen across a lesion, where a clinician wishes to observe or document the condition of a body lumen during an invasive procedure, an imaging instrument may be retracted proximally ("pulled-back") to scan the lumen in order to display real-time images of the lesion and lumen wall. Such a pull-back scan may take more than one and a half minutes. In many instances a clear saline wash solution is used to remove or dilute blood within the lumen in the region around the imaging apparatus in order to provide better visualization of the vessel walls. However, such a saline wash introduce large volumes of fluid into the patient. Saline does not carry as much oxygen as blood, so that excessive amounts may reduce oxygenation within a patient's tissues, and increasing blood volume may stress the heart, so that excessive washing may be harmful to a patient. High intensity illumination within a body lumen, using visible light or other radiation, including ultrasound radiation, may be used in an attempt to improve the quality of images obtained in saline and to obtain better images through blood or partially-diluted blood. However, intense radiation within a body lumen may be harmful to a patient's tissue, particularly if the tissue is exposed to such radiation for a minute and a half or more.

As a result, prior art methods present clinicians with the poor choices of either limiting illumination intensity and exposure time in consideration of patient health and comfort, resulting in poor quality images, or ignoring patient health and comfort by using higher intensity illumination and longer exposure times, resulting in possible tissue damage. Accordingly, devices and methods for obtaining high quality images from within a body lumen while minimizing damage and stress to the patient are desired.

SUMMARY

The invention provides systems, devices and methods for acquiring, storing and playing back image information taken from within a body lumen. The systems, methods and devices provide for decoupling the acquisition scanning rate and the playback rate so that, for example, images may be viewed more slowly than they are acquired, and regions of interest within a body lumen may be re-inspected by replay of the stored image without the need for re-acquisition of a image information, thereby reducing trauma to the patient and making clinical procedures more efficient. In addition, it is possible to selectively view images of some regions within a body lumen without the need for viewing images of other regions. The methods of the invention are suitable for use with any imaging method, including ultrasound and optical imaging (including infrared, visual, and other wavelengths of optical information). For example, the methods are suitable for use with an OCT imaging system.

Systems embodying features of the invention enable acquisition of image information from within a body lumen, and include an imaging information acquisition component (acquisition component) configured to detect image information from within a body lumen, an image information storage component (storage component) configured to store image information in an electronically readable form, and an image information playback component (playback component) configured to read stored image information and to output an electronic signal in accordance with it. A signal in accordance with image information is a signal that is proportional to the image information, or can be decoded to provide a representation the image information, and/or that can be used to display, print, or otherwise make use of the image information. Image information may be transferred from one component to another, e.g., from the acquisition component to the storage component, by transmission elements configured to convey optical, electrical, or other signals.

In some embodiments, the imaging information acquisition component comprises an IGW. The IGW may be configured to perform a rotational scan so as to acquire imaging information from a plurality of positions within the body lumen, and imaging information may be detected by image acquisition components within a shaft of an elongated intracorporeal instrument; in some embodiments, the imaging acquisition components are configured to rotate within the shaft, which may have windows or aperture configured to pass image information. In some embodiments, the image information comprises optical information. Image information will typically be acquired in discrete image samples detected in sequence, the number of image samples detected per second defining the image acquisition rate.

The imaging information storage components of systems and devices embodying features of the invention may be any form of memory storage device, including sequential memory storage devices and addressable memory storage devices. Memory storage devices include such devices as magnetic memory disks, magnetic tapes, random access memory chip devices (RAM), magnetic/optical memory disks, and optical memory disks such as laser disks and compact disks (CDs), including compact disk read-only memory disks (CD-ROMs) and readable/writable CDs (R/W CDs). Addressable memory storage memory devices may be temporary or may be permanent memory storage devices, including RAM chips, hard drives, tapes, floppy disks, ZIP disks, and CDs.

The systems and devices of the invention include a playback component. A playback component provides a signal based on the stored image information. Such a signal may be, for example, a video signal configured to provide a video image on a video display monitor or on the print-out of a printer. In systems and devices embodying features of the invention, the playback component may include a video display such as a video monitor, and may include a printer.

Playback of imaging information may include display of images on video displays or on hardcopies of images produced by a printer. Such display may be sequential, or may display images out of sequence. In embodiments of the invention, non-sequentially displayed images may omit intervening images between displayed images, or may display images in reverse order with respect to the order of acquisition, or may combine, by adding, subtracting, averaging, enhancing or filtering an image or multiple images for display of a modified or composite image, using either analog or digital methods.

In some embodiments of the invention, the systems and devices include a control component. A control component may be a dedicated circuit effective to control the operation of the a component or a device, and may include a digital signal processing (DSP) chip which may be hard-wired, preprogrammed, or programmable. A control component may also, or instead, include a central processing unit, and may be a computer. In some embodiments, the control component and the storage component comprise a computer with a hard-drive.

Systems and devices embodying features of the invention may be configured to acquire, store, and play back imaging information acquired from within a body lumen. For example, an acquisition component may record image information as a continuous analog signal, which may be stored in amplitude modulated form or frequency modulated form, including pulse-code modulated form.

Alternatively, or in addition to an analog signal, an acquisition component may record image information in digital form. For example, an acquisition component may be configured to sequentially record discrete image samples in an addressable memory device in an electronically-readable form and to play back stored imaging information in discrete units sequentially in time at a playback rate. Play back components may include an electronic device configured to locate an address in an addressable memory storage device, which may be a digital central processing unit.

In some embodiments of the systems, methods and devices embodying features of the invention, imaging information is detected in analog form at an acquisition rate or as discrete image samples in a sequence at an acquisition rate, stored, and played back at a different rate than the acquisition rate. For analog data, such as a tape drive, the tape may be replayed at a different speed than was used during acquisition. For digital data, for example, the playback rate may be varied by using a different timing speed to gate the output of the digital data, or by replaying the image data multiple times before going on to succeeding images. Play back rates may be positive (in ascending order with respect to the order of the acquisition sequence); negative (descending order with respect to the order of the acquisition sequence); lesser than the acquisition rate; equal to the acquisition rate; or greater than the acquisition rate.

A method of the invention for acquiring, storing, and playing back imaging information acquired from within a body lumen includes the steps of acquiring imaging information from within a body lumen in discrete samples detected sequentially in time at an imaging acquisition rate with an elongate intracorporeal instrument positioned at least in part within the body lumen; storing the imaging information in an addressable memory device in an electronically-readable form; and playing back stored imaging information in discrete units sequentially in time at a playback rate.

Imaging information that is played back may be used to form a video image for display to an observer or for printing. The playback of imaging information may begin at any memory address, corresponding to any location within the scanned region, so that an observer may view a video image from any desired location within the scanned region of the body lumen.

In contrast to prior art systems which display images essentially in real-time, image acquisition, storage and playback systems and devices embodying features of the invention provide systems and devices which play back image information at a rate different than the acquisition rate. For example, slow playback of a rapidly acquired image scan offers the advantages of reducing possible patient trauma by reducing the duration of the procedure, and avoiding the need for repeat imaging of a region, while improving the ability of the physician to carefully inspect the image.

DETAILED DESCRIPTION OF THE INVENTION

Figure 1:
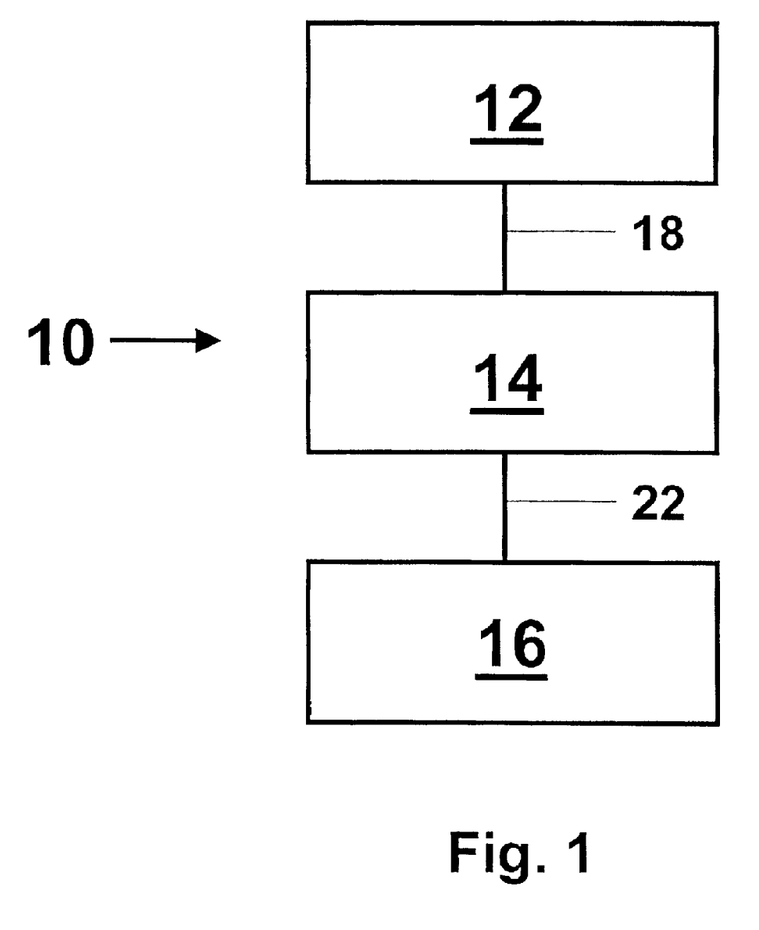
FIG. 1 illustrates a system for acquiring, storing and playing back image information embodying features of the invention.

FIG. 1 illustrates a system 10 embodying features of the invention comprising an imaging information acquisition component 12, an imaging information storage component 14, and an imaging information playback component 16. Imaging information acquired by acquisition component 12 is transferred to storage component 14 via connection 18, and imaging information read-out from storage component 14 is transferred to playback component 16 via connection 22. Connections 18 and 22 are image information transmission elements effective to operably connect components of the system 10.

Connections 18 and 22 are effective to transfer image information from one component to another, and may include wires, cables, optical fibers, waveguides, or other suitable transmission element configured to convey optical, electrical, or other signal. In some embodiments of the invention, connections 18 and 22 are configured to pass information in only one direction; in other embodiments, one or both of connections 18 and 22 are configured to pass information in two directions effective that storage component 14 may pass information to acquisition component 12 as well as receiving information from acquisition component 12; and playback component 16 may pass information to storage component 14 as well as receiving information from storage component 14. Such bi-directional transfer of information is effective to provide timing signals, communicate buffer capacity, transfer interrupt signals, and to carry other information useful for efficient information transfer and for management and coordination of such information transfer.

Acquisition and storage are configured to be performed at defined rates, the storage rate generally being at least as fast as the acquisition rate (buffer memory may be used to temporarily store acquired information in those instances where the storage rate is less than the acquisition rate). Playback is configured to be performed at a defined playback rate. Such rates may be adjustable and under user control, and, in some embodiments of the invention, a playback rate maybe less than an acquisition rate effective to display images more slowly than they were acquired. In this way, images may be acquired as rapidly as possible, to reduce the time that a body lumen may be exposed to illumination and to saline washing, while an observing clinician may inspect the images at a desired pace. Inspection of stored images may begin with an image at any desired position within a body lumen, and need not begin with images of the initial imaging position. Storage of images in addressable memory allows an observer to select desired images to view, so that stored images may be inspected in order or out of order. Digitally stored images may be viewed by accessing the images via their addresses in the memory storage device, such as by beginning to read from a particular track and sector of a hard-drive. Analog images may be viewed by accessing the images via their linear location along a tape, or by beginning to read from a particular track on a CD.

Figure 2:
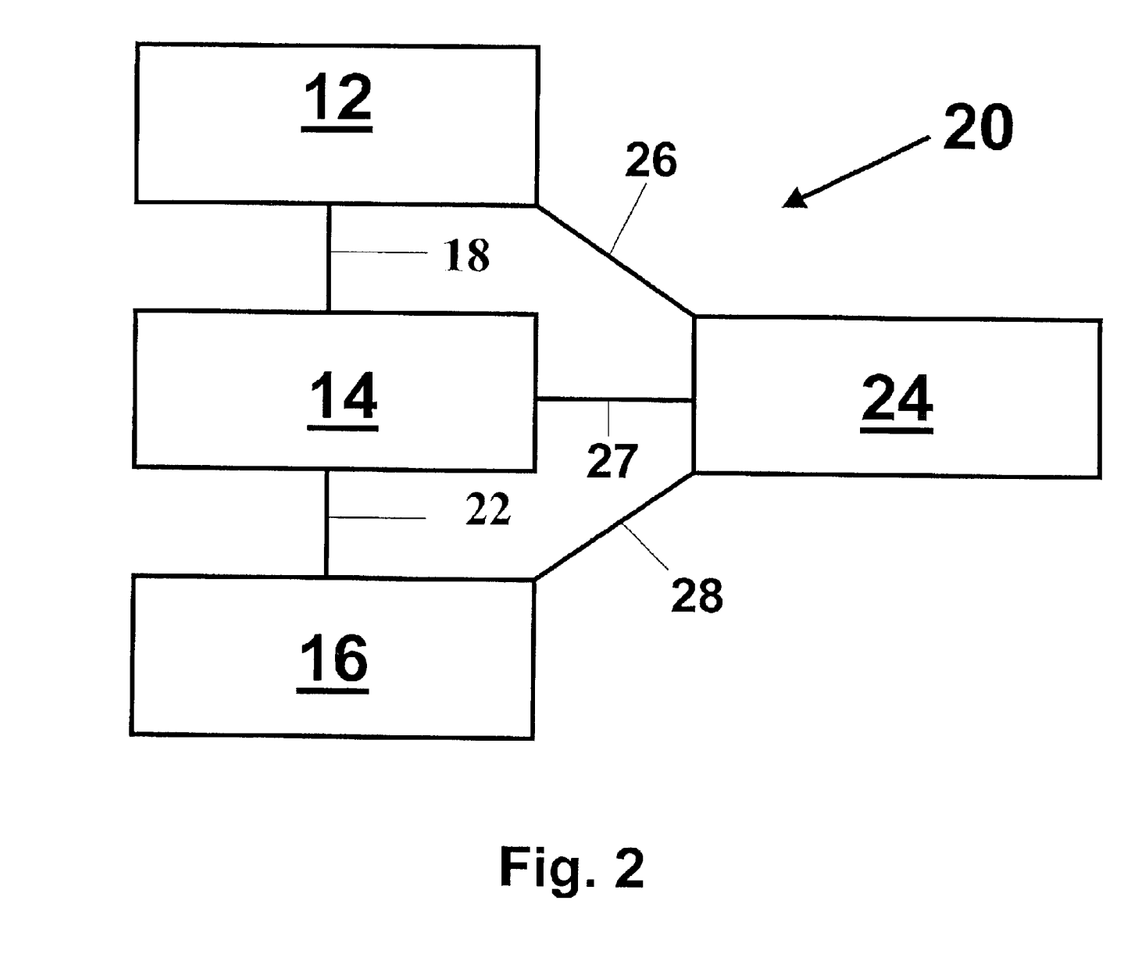
FIG. 2 illustrates a system embodying features of the invention with a separate control component.

FIG. 2 illustrates a system 20 embodying features of the invention comprising an imaging information acquisition component 12, an imaging information storage component 14, an imaging information playback component 16, and a control component 24. As in the system illustrated in FIG. 1, acquisition component 12 is connected to storage component 14 by connection 18, and storage component 14 is connected to playback component 16 via connection 22. Control component 24 is connected to all other components by connections 26, 27 and 28.

Figure 3:
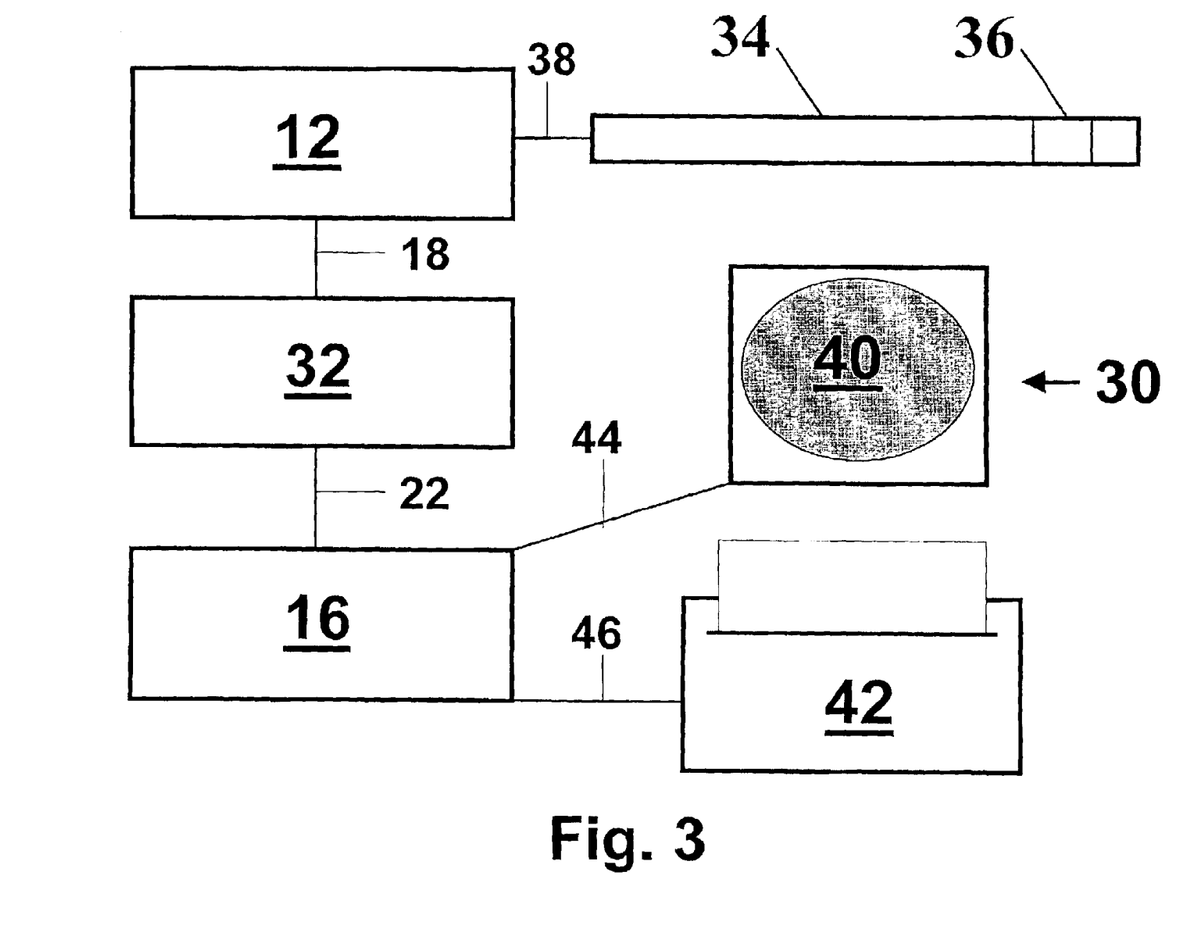
FIG. 3 illustrates a system embodying features of the invention having an IGW, a computer configured to store image information and to control components of the system, a video display and a printer.

FIG. 3 illustrates a system 30 embodying features of the invention including an intracorporeal imaging instrument. The intracorporeal imaging instrument in the embodiment shown in FIG. 3 is an IGW configured for obtaining an image from within a body lumen such as a blood vessel. Other intracorporeal imaging instruments suitable for use with a system 30 embodying features of the invention include imaging catheters, endoscopes, and other instruments. System 30 includes an imaging information acquisition component 12, an imaging information storage and control component 32, and an imaging information playback component 16. Acquisition component 12 is connected to an IGW 34 having a window 36. Radiation may pass through window 36 effective that features of a body lumen may be illuminated, and image information comprising radiation reflected and emitted from the body lumen may be acquired by IGW 34. The imaging information may be carried to the acquisition component 12 via connection 38. In some embodiments, illuminating radiation also passes along connection 38 for transmission by IGW 34 to a body lumen. Such imaging devices typically use an optical fiber to carry optical radiation.

Optical radiation is suitable for imaging within a body lumen. The terms "light" and "optical radiation" are used herein to mean electromagnetic radiation including but not limited to visible light, infrared radiation, ultraviolet radiation, and other radiation. Optical radiation may include radiation having a wavelength in the range of between about 0.1 to about 3 micron, and may particularly include radiation having a wavelength between about 0.75 micron to about 2.5 micron, or radiation having a wavelength between about 0.1 micron to about 1 micron.

In addition to optical radiation, acoustic radiation such as ultrasound may be used to obtain image information from within a body lumen. Methods for using ultrasound, including methods for storing and retrieving digital representations of ultrasound images from a storage system, are discussed in U.S. Pat. No. 6,300,961 to Finger et al.

Ultrasound image data (also termed acoustic image data) includes data that has been acquired using the transmission of acoustic energy, and has been used to generate an image or audio output in one or more of various modes, such as B-mode, M-mode, color Doppler mode (velocity, variance or energy), spectral Doppler mode (spectrum, derived waveform or audio) and other modes. Ultrasound image data includes primary acoustic data from a beamformer (such as in-phase and quadrature data or real value data), fundamental or harmonic frequency based data, or acoustic data at various stages of processing (e.g. detected data, filtered data, weighted data, thresholded data, video data (compressed or uncompressed), combined data, and other processed data derived from acoustic data from the beamformer). Ultrasound image data includes, for example, beamformer data (ultrasound image data provided by a beamformer) and harmonic data (ultrasound image data associated with harmonic frequencies of transmitted fundamental frequencies).

System 30 also includes the display devices video monitor 40 and printer 42. The monitor 40 is connected to playback component 16 by connection 44; printer 42 is connected to playback component 16 by connection 46. As discussed above with respect to connections 18, 22, 26, 27, 28 and 38, connections 44 and 46 may be configured to pass information along their lengths in either or both of two longitudinal directions.

Information transferred along any of the connections discussed with regard to the embodiments of the invention may be digital or analog information, and may be carried by electrical signals, optical signals, acoustic signals, or other suitable signals and combinations of signals. Accordingly, in any embodiment of the invention, a connection may comprise a wire connection, including braided wires, twisted-pair wires, ribbon cables, co-axial cables, video cables, audio cables, and other wires or cables; a circuit board trace, jumper, or other circuit board connection; a waveguide; an optical fiber; or other signal transfer component or combination of components.

An IGW useful in systems, devices and methods of the invention may be, for example, an optical IGW or an ultrasound IGW. Examples of imaging endoscopes, guidewires and catheters are described in U.S. Pat. Nos. 5,321,501 and 5,459,570 to Swanson et al., and U.S. Pat. No. 6,134,003 to Tearney et al. Catheters adapted for optical imaging using non-visible light may be used in the systems, methods and devices of the invention. Examples of optical imaging catheters are described in U.S. Pat. No. 5,935,075 to Cassells et al. An IGW useful in systems, devices and methods of the invention may be located for use within a body lumen either alone or with the use of a guiding instrument such as a guiding sheath, and may be used alone or in conjunction with other intracorporeal instruments such as a catheter. An example of a guiding sheath for use in aiding the internal placement of intracorporeal instruments is discussed in Buck et al., U.S. Pat. No. 6,004,280.

Devices and methods for making and using intracorporeal imaging instruments are disclosed in co-owned application Ser. No. WWW "Methods for Forming an Optical Window for an Intracorporeal Device and Joining Parts," to Webler et al., application Ser. No. XXX, "Optical Guidewire Having Windows or Apertures" to Jalisi et al., application Ser. No. YYY "Rotatable Ferrules and Interfaces for Use with an Optical Guidewire," to Webler et al., and application Ser. No. ZZZ "Sheath for Guiding Imaging Instruments," to Webler et al.

An optical pathway provides a route for optical radiation to pass, to be carried or to be transmitted from one location to another, and so provides optical access between such locations. An "optical pathway" may be a window, aperture, plurality of windows or apertures, an optical fiber, a void, or any other object or material through which optical radiation is able to travel. Optical communication includes passage of optical radiation between objects or between locations, where such radiation is present, or includes a pathway capable of effecting such passage of optical radiation in the event that optical radiation is not present. Typically, the components of an optical assembly, which may include an optical fiber and a lens or a prism, are in optical communication with each other. In addition, an operable optical connection between an optical fiber and a window or aperture means a connection effective so that at least some optical radiation passing through the window or aperture may enter or have been emitted from the optical fiber. There need not be physical contact between objects for there to be optical communication between the objects or locations.

An "optical fiber" is a thin elongated material effective to carry optical radiation from one location to another (e.g., from one end of the optical fiber to the other end). Optical fibers are typically made of glass which has been heated and stretched into very thin strands. Such glass fibers may be coated ("clad") so as to improve their optical performance and mechanical properties. Multiple strands of glass fibers may be loosely intertwined or bundled together, or may be packed and glued or clad together, to form fiber optic cables or optical assemblies. The term "optical fiber" is used herein to include a single optical fiber, a plurality of optical fibers, and an optical fiber assembly. Thus, an "optical fiber" may be a single strand (whether clad or not) or multiple strands of optical fibers, however clad, joined, glued or bundled together.

In some embodiments of the invention, the a window of an IGW may be made up of a plastic or a combination of plastic materials, a resin, and other materials and combinations of materials. Thus, the window may be made of acrylic, polycarbonate, nylon, Teflon®, polyethylene terephthalate (PET), tensilized PET, resins, or blends or combination f of these ingredients.

Methods and instruments for acquiring, and retrieving optical imaging information may be found, for example, in U.S. Pat. No. 6,317,152 to Hobson et al., entitled "Digital Video Recording System"; U.S. Pat. No. 6,249,551 to Yamaguchi, entitled "Video Playback Method and System for Reducing Access Delay"; U.S. Pat. No. 6,185,367 to Keery et al., entitled "Apparatus and Method for Storing and Reproducing High-Resolution Video Images"; U.S. Pat. No. 4,918,523 to Simon et al., entitled "Digital Video Formatting and Transmission System and Method"; U.S. Pat. No. 4,857,990 to Horgan, entitled "Digital Video Storage"; and U.S. Pat. No. 4,755,889 to Schwartz, "Audio and Video Digital Recording and Playback System."

In the following discussion, optical imaging information will be used to exemplify imaging information. It should be understood that, whether discussed supra or infra, the same considerations regarding data acquisition, filtering, manipulation, and storage apply to ultrasound image information as well as to optical image information; and that devices and methods describe in terms of optical radiation, optical illumination, optical intensity, or similar terms may also be applied to ultrasound, analogously in terms of ultrasound energy, applying ultrasound energy to an object or region of interest, and ultrasound intensity.

In general, imaging information may be acquired, stored, and played back using the following general strategy. A device sensitive to optical or ultrasound radiation, such as a video camera, is placed within a body lumen and directed at a region of interest. In analog acquisition, the camera continuously views the region of interest and generates image signals of the region which are transmitted to a storage device, such as a tape or compact disk. The signal may be filtered or otherwise manipulated before being recorded by the storage device. Upon playback, the recorded signal is delivered to a display device such as a video display for inspection by an observer. The playback device may allow asynchronous playback, as by starting playback at a position after the beginning of the recorded image stream.

In digital acquisition, the camera may continuously view the region of interest and generates video images of the region at a predetermined frame rate. A frame grabber converts the video images produced by the camera to a digital signal. A processor processes the digital signals, e.g., by filtering, subtracting background, or enhancing contrast, and the processed signal is recorded. The storage component may compress the image information for more efficient storage. The video image is stored together with time and position information, which may be implicit (e.g., by the address of the information ) or explicit (e.g., separate memory locations storing identifying information related to each pixel). A video playback capability allows the memory location where an image of interest is stored to be directly accessed to retrieve the image. The playback system enables access of the memory to playback any desired time and position so that an image of interest can be reviewed without having to scan video images in the acquisition sequence. In some embodiments, accessing the memory may be done without interrupting the processor's processing of new digital signals for currently acquired video images.

Typically, image information will be acquired by a rotating scan of the interior of a body lumen. In a rotating scan, an imaging element, such as a lens or prism attached to an optical fiber mounted within an IGW with a window or aperture may be rotated rapidly to provide the imaging element with optical access to the region on all sides (360° around the window or aperture) of the IGW. A rotation rate of about 20 to about 30 rotations per second (RPS) may be required to form a stable two-dimensional image. As the imaging element is rotated, it may also be moved in a longitudinal direction, so that the region directly opposite the imaging element follows a spiral-shaped path within the body lumen. The rotational and longitudinal movements may be configured so that the spiral-shaped path covers the entire region of interest within the body lumen, and is effective to provide image information without gaps. In some embodiments, the longitudinal movement and the rotational movement are coordinated so that there is overlap in the regions covered by the image information acquired during sequential rotations.

In some embodiments of the methods of the invention, the method of scanning used is a "pullback" scan, in which image information is acquired while an imaging instrument moves from a distal position within a body lumen to a more proximal one (distal and proximal being taken with respect to the point of insertion into a patient's body). Thus, prior to performing pullback scan, an intracorporeal imaging instrument is positioned within a body lumen distal to a region of interest, such as a lesion. Then, the imaging instrument is retracted proximally while the imaging elements are rotated, in order to scan the length and circumference of the body lumen, thereby to obtain imaging information pertaining to the lesion. Such a scan allows a clinician to observe or document the condition of a body lumen during an invasive procedure.

Image information may be acquired in analog form or in digital form during a scan, and may be written to a storage component in analog form or in digital form. For example, image information may be collected as a continuous stream of light intensity values, polarization measurements, or other measurement of optical radiation. Alternatively, image information may be collected as a series of discrete samples. Such samples may include a single datum or may include information from multiple measurements or types of measurements. For example, in some embodiments of the invention, a single sample may record the light intensity at a particular location and at a particular time during a scan. In other embodiments, such as scans recording spectral or chromatic information, a sample may include light intensity, color, polarization, and other information as well. Information pertaining to the intensity of a signal at a particular wavelength, or range of wavelengths, is often termed "luminance" data; information pertaining to color is often termed "chrominance" data.

Analog data for a single optical wavelength or wavelength range may be stored as a continuous stream of intensity measurements for that wavelength range. Where color information is desired, as, for example, where it is desired to reconstruct a color image from the recorded data, three analog signals representing the signal intensity for each of three wavelength ranges of optical radiation may be recorded on three different channels, tracks, or addresses in the storage component. Alternatively, combinations of the signals may be stored and deconstructed upon playback (e.g., using a scheme similar to the scheme described below for digital data storage). Analog data may be converted to digital data using an analog-to-digital converter.

Digitally recorded image information includes data pertaining to the optical intensities observed at a particular region for a particular time. Such data defines a picture element, or pixel, that is a single unit of the composite digital image made up of the ordered combination of all the pixels. A digital image is formed of a finite number of pixels; the greater the number of pixels, the greater the resolution of the image, and the finer the detail that may be observed in the image. Information recorded for each pixel may include either or both of luminance and chrominance information. For example, where monochrome intensity data is recorded for a range of optical wavelengths Y, color information may be acquired using the intensities for other ranges of optical wavelengths R and B and color information stored by recording values of Y, R minus Y, and B minus Y for each pixel. Such information may be stored in an addressable memory device for later playback.

Data for an individual digital data sample is acquired over a brief period of time. For example, in some embodiments of the invention, the brief period of time may be as short as one millisecond; in other embodiments of the invention, the brief period of time may be as short as one microsecond; in still other embodiments of the invention, the brief period of time may be shorter than one microsecond. The duration of such a period of time may be determined by the types of measurements desired and the information to be derived form such measurements, or may be determined by the characteristics or limitations of the instrument or system used to make the measurements, or of the environment in which the measurements are taken.

Samples are acquired at a rate termed the acquisition rate, defined as the number of samples acquired per second. As is well known, and as described by the Nyquist theorem, it is possible that spurious low-frequency signals may be created as an artifact of digital sampling through a process termed "aliasing". In order to avoid aliasing, sampled data is typically filtered with a low-pass filter having a cut-off frequency that is half or less, often about one fourth, typically about one fifth, of the acquisition rate. The Nyquist theorem applies to digital data, and is not directly pertinent to analog data. However, recording instruments and recording media have finite bandwidth, so that some frequency components of a recorded signal may be attenuated to a different extent than other frequency components, resulting in the artifactual distortion of the recorded signal as compared to the signal of origin. For this reason, it is advisable to filter analog data as well as digital data before storage, using a filter with a known and regular frequency response roll-off. By providing a sharper and more predictable range of frequencies, such filtering provides a recorded signal that is closer to the original than might be obtained were the data to be recorded without filtering by a recording instrument onto a recording medium.

Data may be stored as amplitude modulated (AM) signals, frequency modulated signals (FM), including pulse-code modulated signals (PCM) as are used in, for example, laser disks. In addition, there are multiple formats for digital storage of image information, including bit-mapped information, MPEG format, JPEG format, and others, which may be suitable for the practice of the invention. Data may be stored in compressed or uncompressed formats. Digital image information may be formed and stored using a "frame grabber" such as are commercially available for operatively mounting in a computer.

Prior to storage, or upon playback after storage, image information may be manipulated to enhance contrast, highlight features, remove noise and artifacts, subtract background or interfering signals, smooth or average signal information, combine signals or images to provide composite signals or images, or otherwise changed to maximize the useful information content and minimize spurious or unwanted signals. Data may be filtered by either analog or digital filtering techniques, and may be combined, subtracted, added, enhanced, for example by digital contrast enhancement, signal averaging, background subtraction, or other techniques known in the art. Where OCT is used, as discussed above and described in, e.g., Tearney et al., optical information from within a body lumen may be combined with optical information from a reference optical pathway and used to provide image information. Such manipulation is in addition to any filtering which may be applied to the image information. Such manipulation may be accomplished by analog circuitry, digital signal processing (DSP) elements and methods, methods utilizing computer software, or other methods and combinations of methods. Analog data and digital data may be manipulated before playback (including upon acquisition or before storage) or, upon playback, before being displayed.

An imaging acquisition, storage and playback system embodying features of the invention may include a controller, such as a central processing unit or a computer configured to control any or all of image acquisition, manipulation, storage, and playback. A controller may include a single microprocessor, multiple microprocessors, numeric coprocessors, dedicated memory such as buffer or cache memory, and may be programmed to respond to or to execute instructions coded in memory or hard-wired into the device. A controller may be configured to control data transfer between components of an image acquisition, storage and playback system, to control aspects of acquisition, storage or playback so as to accommodate environmental conditions or patient characteristics, to serve as part of an interface between such a system and other systems or between such a system and an operator, and other functions or combinations of functions. An imaging acquisition, storage and playback system embodying features of the invention, optionally including a controller as described above, may include sampling and selection components to select signals and images according to predetermined criteria or according to operator command.

An imaging information storage component may include electronic memory such as random access memory (RAM), dynamic random access memory (DRAM), static random access memory (SRAM), or other electronic memory, which may be synchronous or non-synchronous; magnetic memory such as a tape, floppy disk, bubble memory or hard drive; optical recording memory such as a CD-ROM; magneto-optical memory such as a readable/writable CD-ROM; other memory devices, and combinations of these memory devices. Image information may be stored in compressed or uncompressed form, and may be stored as uncoded data or may be coded before storage. Data storage for images are described, for example, in U.S. Pat. Nos. 4,857,990; 6,185,367; 6,300,961; and 6,317,152 cited above.

A playback component includes devices and methods for accessing desired image information stored at a particular memory address or range of addresses, reading it, and displaying the stored image. The memory address may be a virtual address or may correspond to a physical location, such as a position along a tape of on a disk. Playback components are commonly known and are found in such commercial products as tape players, VCR machines, computers with disk drives, CD players, and so forth, as well as in clinical and scientific instruments. A playback component may include a display, such as a computer monitor or other video display, which may be in color or monocolor. A playback component may also include a hard-copy print-out of the image information, as may be provided by a printer, such as a laser printer, ink-jet printer, or other printer. Playback and display systems are described, for example, in U.S. Pat. Nos. 6,185,367; 6,249,551; and 6,300,961 cited above.

In some embodiments of the invention, imaging information is played back at a rate different than the acquisition rate. Thus, while imaging information may be acquired at one frequency suitable for a rapid scan to minimize the exposure of internal tissues to radiation and to minimize the amount of saline introduced into a patient to provide better imaging within a body lumen, the imaging information may be played back at a slower speed to allow a human observer, such as a physician treating the patient undergoing an intracorporeal procedure, to observe the images more carefully than would be possible were the images to be replayed as rapidly as they were acquired.

Playing back image information at a rate different than the acquisition rate uncouples the rate of presentation to a clinical observer from that of acquisition. This allows the rapid collection of images, reducing patient exposure to possible trauma from high intensity illumination and extended washing of an internal lumen with saline solution. Image storage also avoids the need for repeated manipulation and movement of an intracorporeal device within a body lumen, reducing risk of physical trauma caused by contact between the instrument and the lumen itself. This is in contrast to prior art systems which display images essentially in real-time, where a pull-back may last in excess of a minute and a half. In addition, since the physician has control of the image playback, and can view the image as many times as desired at a rate that allows careful inspection of the image, the usefulness of the acquired images is enhanced.

Image acquisition, storage and playback systems embodying features of the invention may be particularly useful where the image acquisition components use OCT imaging techniques. Images acquired using OCT imaging may be susceptible to degradation by light scattering due to blood cells and other interfering environmental conditions, which may limit the depth of penetration into tissue. Such image degradation may be minimized by injecting saline or other relatively transparent fluid to dilute or replace blood within a body lumen. However, if the data collection time, and so the required duration of saline injection, is too long, then a patient's heart becomes deprived of oxygen and nutrients for too long a time, which may result in pain, conduction anomalies, arrhythmia, and other adverse or undesirable events. By keeping short the duration of image data collection, it becomes more practical and safer to inject a non-scattering solution directly into the vessel to replace the blood and thus increase the imaging depth during OCT image data collection. Additionally, by minimizing the duration of saline injection, the volume of the injected fluid will be minimized. Excessive fluid volume may increase the workload of the heart, causing pain, leading to more rapid heart failure and other adverse events.

Dilution of the blood may be adequate to extend the imaging depth to improve penetration and image quality such that the images reliably contain adequate structural information about the walls of a body lumen. For example, for cardiovascular applications, the improved imaging depth of penetration that results from dilution is useful to provide structural information about atheromas or other blood vessel lesions of interest. In some embodiments of the methods of the invention, fluid is injected through a guiding catheter. Saline or other relatively transparent fluid may be introduced into a body lumen in the region adjacent the imaging components by other methods. The preferred injection fluids are saline type injection solutions configured to be compatible with the cardiovascular system. For example, standard clinical saline solution, and other saline solutions with osmolarity and pH similar to that of blood, are suitable. Oxygenated fluids, including oxygenated saline, may be used. In addition, fluorocarbon solutions adapted to carry more oxygen than solely water-based solutions may also be used.

Fluid flow rates as high as 3 cc/sec may be required to completely replace the blood in a coronary vessel, for example. However, complete replacement of the blood by the injected solution may not be required; in some embodiments of the methods of the invention, it is sufficient that 50% or more of the blood present in a region adjacent the imaging components be replaced. In other embodiments, more than 70%, and in still other embodiments, more than 90% of the blood present in a region adjacent the imaging components may be replaced by injected solution.

Image information acquired during a scan such as a pull-back scan may be provide images of a length of the lumen. Images may be acquired over lengths of up to about 15 cm, particularly up to about 10 cm, more particularly up to about 7 cm. The longer the length of the scanned region, the longer the duration of the scan, and the more image information that must be acquired and stored. Where data storage capacity is limited, or a limiting factor, decreasing the image resolution allows the amount of data stored to remain constant while image length is increased. For example, for a blood vessel, limiting the data collection to a region extending over a 7 cm length of vessel is a suitable length.

In some embodiments of the invention, saline injection may be automatically controlled and monitored during collection of image information. In other embodiments, injection of saline may be controlled and monitored by an operator during collection of image information.

One measure of the quality of an image is the signal to noise ratio. Noise, which includes the background detector output that is present in the absence of a desired signal, may become a significant proportion of the signal from an optical detector under conditions of low illumination. Background noise levels are generally independent of the illumination level. Thus, increasing illumination intensity may increase the desired signal (due to increased reflectance) without substantially raising the background. For this reason, high intensity optical radiation may be used in order to obtain a high signal to noise ratio OCT image at the maximum imaging depth.

However, high intensity optical radiation often results in increased tissue heating and other deleterious effects from the increased light energy. Rapid image data collection is effective to limit the duration of exposure to high intensity radiation that any portion of the tissue is exposed to, and therefore to limit any heating effects. Alternatively, with manual longitudinal translation during an imaging scan, the intensity of the illumination could be reduced or the optical radiation could be blocked at a controlled rate in order to limit tissue heating. Where the intensity of optical radiation is reduced to minimize deleterious tissue effects, signal averaging and other image enhancement techniques may be used in order to produce the best image quality.

Analog imaging information may be played back at a different rate than the acquisition rate. For example, analog data stored on a tape is acquired with the tape running across the write heads at a substantially constant tape-speed. Playback of such analog data is similarly effected by running the tape past read-heads; playing back a tape at a different speed than the acquisition tape-speed will result in a playback rate that is different than the acquisition rate. Thus, a tape containing image information from a scan from within a body lumen that is played back more slowly than it was run during acquisition of an imaging scan will provide a representation of the scanned images that is slower than the acquisition. Thus, where analog data is stored on a tape, or floppy disk, or other medium, the playback rate may be varied by replaying the tape, disk, or other medium at a different speed than was used during acquisition. Images may be presented in reverse temporal order by playing a tape, disk, or other recording device in the direction opposite to the acquisition direction.

Digital data may also be played back at a rate different than the acquisition rate effective to provide an observe with usable image information even from data acquired at a rate too fast for effective human interpretation. For digital data, for example, the playback rate may be varied by using a different timing speed to gate the output of the digital data, or by replaying the image data multiple times before going on to succeeding images.

While particular forms of the invention have been illustrated and described, it will be apparent that various modifications can be made without departing from the spirit and scope of the invention. Accordingly, it is not intended that the invention be limited except as by the appended claims.

What is claimed is:

1. A system for acquiring imaging information from within a body lumen, comprising an imaging information acquisition component comprising an imaging guidewire (IGW) configured to detect image information from within a body lumen by performing a rotational scan effective to acquire imaging information from a plurality of positions within said body lumen, an image information storage component configured to store image information in an electronically readable form, an image information playback component configured to read said stored image information and to output an electronic signal in accordance with said stored image information, and transmission elements effective to transfer image information between said imaging information acquisition component and said image information storage component and between said image information storage component and said image information playback component.

2. The system of claim 1, further comprising a control component in communication with said imaging information acquisition component, said image information storage component and said image information playback component.

3. The system of claim 1, wherein said IGW comprises a shaft and an image acquisition component configured to rotate within said shaft.

4. The system of claim 3, wherein said IGW comprises a pathway effective to pass imaging information to said image acquisition component configured to rotate within said shaft, wherein said pathway is selected from the group consisting of windows and apertures.

5. The system of claim 1, wherein said IGW comprises an optical IGW.

6. The system of claim 1, wherein said imaging information storage component comprises an addressable memory storage device.

7. The system of claim 6, wherein said addressable memory storage device is selected from the group of addressable memory storage devices consisting of magnetic memory disks, magnetic tapes, random access memory chip devices ("RAM"), magnetic/optical memory disks, and optical memory disks.

8. The system of claim 6, wherein said addressable memory storage device comprises an erasable memory storage device.

9. The system of claim 6, wherein said addressable memory storage device comprises a permanent memory storage device.

10. The system of claim 1 wherein, said image information playback component comprises an electronic device configured to locate an address in an addressable member storage device.

11. The system of claim 10, wherein said electronic device configured to locate an address in an addressable memory storage device comprises a digital central processing unit.

12. The system of claim 1, wherein said imaging information is detected in discrete image samples in a sequence, wherein the number of image samples detected per second comprises an image acquisition rate, and wherein said stored imaging information is played back in discrete units, wherein the number of units played back per second comprises an image playback rate.

13. The system of claim 12, wherein said image playback rate is configured to be a selectable playback rate selected from the group of playback rates consisting of positive playback rates, wherein a positive playback rate plays discrete image units in ascending order with respect to the acquisition sequence; negative playback rates, wherein a negative playback rate plays discrete imaging units in descending order with respect to the acquisition sequence; playback rates lesser than the acquisition rate; the playback rate equal to the acquisition rate; and playback rates greater than the acquisition rate.

14. The system of claim 12, wherein said playback rate comprises a playback rate lesser than the acquisition rate.

15. The system of claim 1, further comprising a display device.

16. The system of claim 15, wherein said display device is selected from the group consisting of video displays and printers.

17. A method of acquiring, storing, and playing back imaging information acquired from within a body lumen, comprising the steps of:
   a) acquiring imaging information from within a body lumen by rotational scanning thereof in discrete samples detected sequentially in time at an imaging acquisition rate with an elongate intracorporeal instrument positioned at least in part within said body lumen;
   b) storing said imaging information in an addressable memory device in an electronically-readable form; and
   c) playing back stored imaging information in discrete units sequentially in time at a playback rate, wherein said playback rate comprises a rate different than said acquisition rate.

18. The method of claim 17, wherein said playback rate comprises a rate less than said acquisition rate.

19. The method of claim 17, wherein said playback step begins at a memory address selected from the group of memory addresses consisting of all possible memory locations.

20. The method of claim 17, further comprising a step of displaying a video representation in accordance with said stored imaging information.

21. The method of claim 17, wherein said stored information further comprises location information related to corresponding image detection samples, wherein said location information relates to the position within said body lumen at which said image information was detected.

22. The method of claim 20, wherein said step of displaying a video representation comprises displaying a sequence of video images, wherein said sequence is selected from the group of sequences consisting of the acquisition sequence, the reverse acquisition sequence, the acquisition sequence with an omitted image, the reverse acquisition sequence with an omitted image, a sequence comprising an image comprising a sum of at least two images, a sequence comprising a difference between at least two images, a sequence comprising a filtered image, a sequence comprising an enhanced image, and combinations thereof.

23. The method of claim 22, wherein said images have been modified by methods selected from the group consisting of analog methods, digital methods, and combinations thereof.

24. The method of claim 17, wherein said acquiring step is performed in a period of time of less than one minute and a half.

25. The method of claim 17, wherein said acquiring step is effective to acquire images from a length of body lumen about 10 cm in length.

26. The method of claim 17, wherein said acquiring step is effective to acquire images from a length of body lumen about 7 cm in length.

27. A device for acquiring, storing and playing back imaging information acquired from within a body lumen, comprising an acquisition component, an addressable memory component, a playback component, and image information transmission elements operably connecting said components, said acquisition component being configured to record rotationally scanned image information in said addressable memory component in an electronically-readable form at an acquisition rate, and said playback component being configured to play back store imaging information at a playback rate, wherein said playback rate may differ from said acquisition rate.

28. The device of claim 27, wherein said playback rate is variable.

29. The device of claim 27, wherein said addressable memory component comprises RAM.

30. The device of claim 27, wherein said addressable memory component comprises a hard drive.

31. The device of claim 27, wherein said addressable memory component comprises a compact disk.

32. The device of claim 27, further comprising image enhancement and combination means.

* * * * *

UNITED STATES PATENT AND TRADEMARK OFFICE
CERTIFICATE OF CORRECTION

PATENT NO. : 6,947,787 B2
DATED : September 20, 2005
INVENTOR(S) : William E. Webler It is certified that error appears in the above-identified patent and that said Letters Patent is hereby corrected as shown below:

Column 4,
Line 58, delete "of the a" and insert -- of a --.

Column 8,
Line 32, delete "WWW" and insert -- 10/025,334 --.
Line 34, delete "XXX" and insert -- 10/024,986 --.
Line 36, delete "YYY" and insert -- 10/025,515 --.
Line 38, delete "ZZZ" and insert -- 10/025,149 --.

Column 9,
Line 8, delete "the a window" and insert -- the window --.

Column 11,
Line 34, delete "form" and insert -- from --.

Column 15,
Line 28, delete "observe" and insert -- observer --.

Signed and Sealed this

Twenty-eighth Day of February, 2006

JON W. DUDAS
*Director of the United States Patent and Trademark Office*